United States Patent
Wadsworth

[11] Patent Number: 5,902,309
[45] Date of Patent: May 11, 1999

[54] COMPOUND LEVER ACTIVATED ELASTOMERIC BAND CASTRATION TOOL

[76] Inventor: LeGrande D. Wadsworth, 889 Dublin Gulch Rd., St. Ignatius, Mont. 59895

[21] Appl. No.: 09/015,337

[22] Filed: Jan. 29, 1998

[51] Int. Cl.$^6$ .................................................. A61B 17/00
[52] U.S. Cl. ........................................ 606/135; 606/139
[58] Field of Search .................................. 606/135, 137, 606/138, 139, 140, 141, 165

[56] References Cited

U.S. PATENT DOCUMENTS

| | | | |
|---|---|---|---|
| 4,516,574 | 5/1985 | Hewes, Jr. ............................... | 606/135 |
| 4,691,704 | 9/1987 | Wadsworth ............................. | 128/306 |
| 5,207,690 | 5/1993 | Rohrabacher et al. ................. | 606/135 |
| 5,236,434 | 8/1993 | Callicrate ................................ | 606/135 |
| 5,403,325 | 4/1995 | Callicrate ................................ | 606/135 |
| 5,681,329 | 10/1997 | Callicrate ................................ | 606/141 |

*Primary Examiner*—Michael Buiz
*Assistant Examiner*—Kevin Truong
*Attorney, Agent, or Firm*—Keith S. Bergman

[57] ABSTRACT

A tool and method for continuous elastomeric band ligation type castration of larger sexually mature animals with an elastic band that must be enlarged by stretching for placement provides an elongate body having a handle at a first rearward end to aid manipulation and an elastic band supporting yoke at a second forward end. The band supporting yoke provides spaced forwardly extending legs for releasable support of the elastic band at two spaced points. Band stretching mechanism carried by the body provides an elongate stretching rod that releasably interconnects one course of the elastic band carried by the yoke at a third point between the two yoke support points to stretch the band rearwardly responsive to motion of an associated compound lever mechanism to enlarge the medial orifice defined by the elastic band sufficiently to allow the band to pass over the scrotal pouch and contained testicular structure of a large animal. The elastic band is stretched rearwardly through an annular support carrying a fastening clip that is deformed about the band to maintain tension in the band portion extending about the neck of the animal scrotal pouch. Release mechanism disassociates the tool from the elastic band to leave the tensioned band portion about the neck of the animal scrotal pouch at the ligation site.

10 Claims, 2 Drawing Sheets

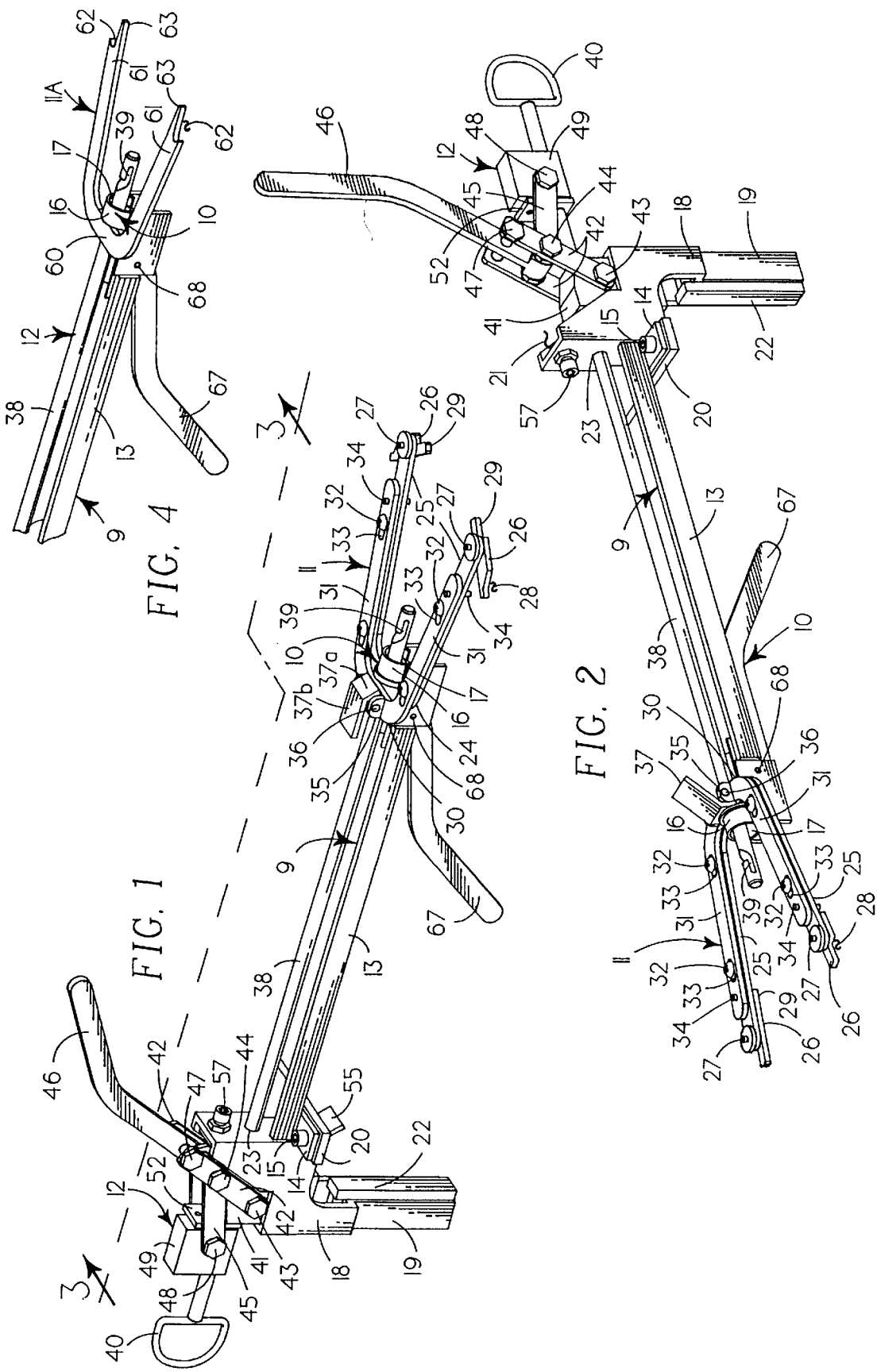

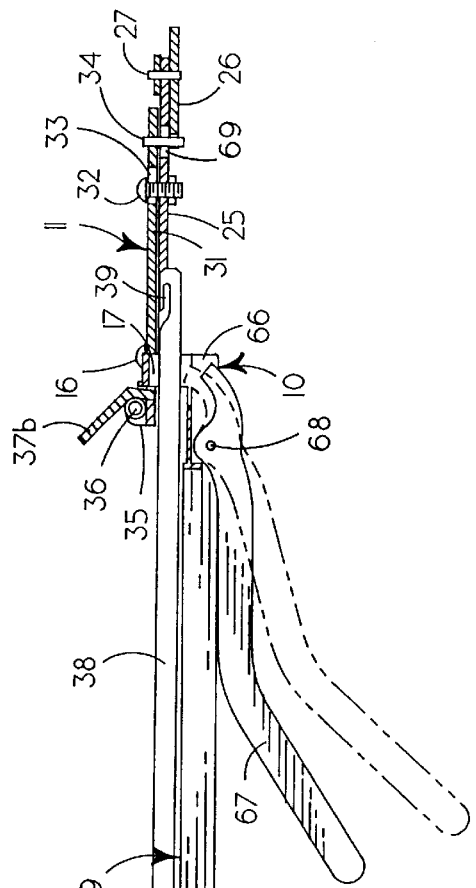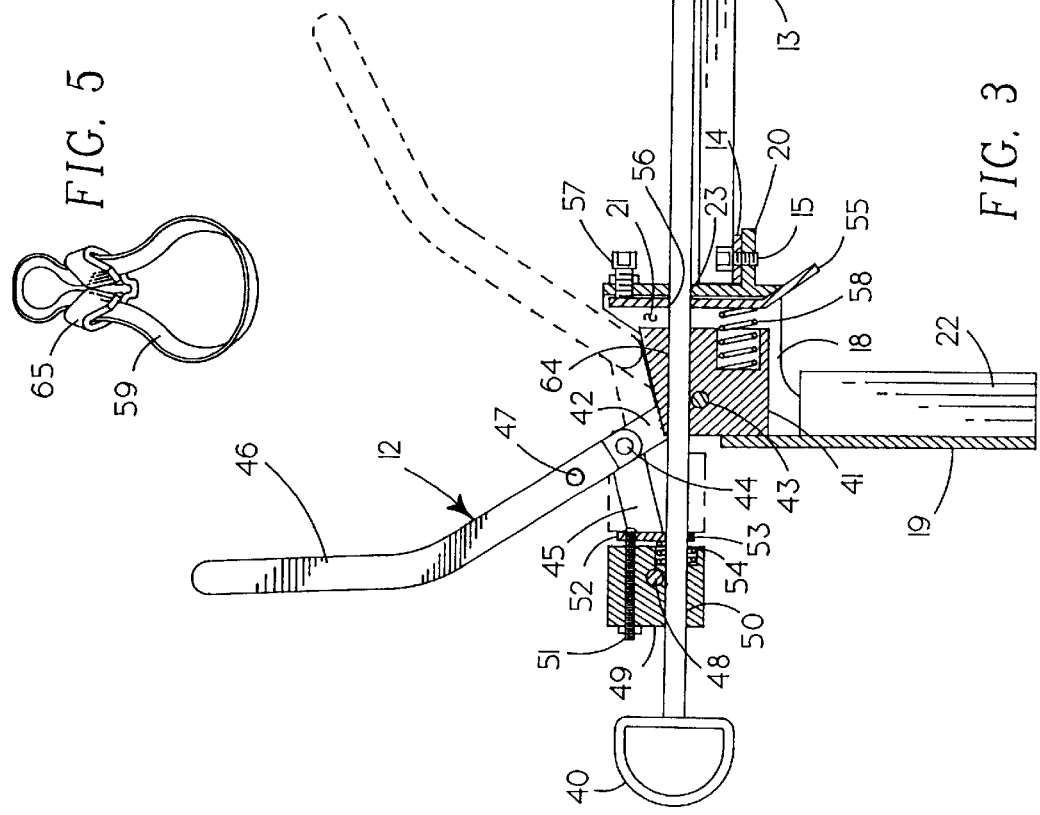

COMPOUND LEVER ACTIVATED ELASTOMERIC BAND CASTRATION TOOL

RELATED APPLICATIONS

There are no applications directly related hereto heretofore filed in this or any foreign country.

BACKGROUND OF INVENTION

1. Field of Invention

This invention relates generally to ligation type castration tools and more particularly to a compound lever activated tool for placement of a small continuous elastomeric band on large mature animals for castration.

2. Description of Prior Art

In modern animal husbandry it has become increasingly common, responsive to market demands, to castrate bovine bulls after their maturity rather than during infancy as heretofore has been common. Such castration by ligation has become popular because of the simplicity of the process and the benefits it provides in avoiding undesirable consequences such as microbal infection, insect invasion, excessive bleeding and the like. Ligation type castration of younger animals has been and is accomplished largely by use of small preformed continuous elastic or elastomeric bands because of the economic viability provided by allowing rapid castration processing that can be accomplished by relatively unskilled persons. The small elastic bands are generally placed by a spreading type tool having two elongate arms pivotally interconnected in their medial portions to allow expansion of a band carried at one end portion of the tool against its elastic bias for placement over the scrotal pouch of the animal with subsequent release. This process works well with juvenile animals that do not have a mature testicular structure of larger size, but it has not been viable with larger animals having mature testicular structure such as bovine bulls, as a small preformed elastic band that would contract to a small enough configuration to provide ligation generally can not be expanded sufficiently, either by its nature or by use of common spreading type tools, to allow passage over the larger testicular structure of the mature animal.

This problem has been recognized in the past and a solution presented by the instant inventor's U.S. Pat. No. 4,691,704 issued Sep. 8, 1987 and U.S. Pat. No. 5,188,637 issued Feb. 23, 1993, whereunder a length of elastic surgical tubing is formed in place, tensioned about the orifice of an animal's scrotal pouch and fastened in its tensed condition by a metallic clip. Though this process provides effective ligation castration of larger mature animals and has been accepted about the world, problems still remain with the process. The instant castration tool resolves some of these remaining problems by providing an easily operated castrating tool for large mature animals that allows placement of a small continuous elastic band that is expanded by tensioning for placement and thereafter foreshortened in its tensed condition about the scrotal pouch orifice by a clip to allow its ligation function.

Ligation castration with continuous preformed bands is easier and less complex than the formation of ligation banding in place and has fewer possibilities for mistakes or errors, to provide a process that requires less care and skill on the part of an operator and generally may be more easily accomplished by unskilled workmen without historical familiarity with the process. Elongate type ligation material that is formed in place also allows parameters for tensioning and band fastening by a clip that may be varied, either accidentally or deliberately by an operator, to provide results that are not necessarily uniform or consistent and may vary sufficiently to make the process inoperative or harmful to an animal. Continuous band ligation material has more fixed parameters determined by the nature and configuration of the banding material itself, which are more independent of an operator's activities. The continuous banding material also is generally more durable than the elongate ligation material formed in place and is less expensive and more easily handled than the elongate material. There are therefore various advantages in using preformed continuous band type elastic material for ligation castrating, when the use of such material is possible.

The nature of the ligation castration process with small preformed continuous band elastic material rather defines the limits of the parameters required for the elastic bands usable for such purpose, and especially their relaxed size and elastic properties. Such bands must be small enough to fulfill their ligation purpose of providing sufficient elastic force or bias after placement and fastening about the neck of the scrotal pouch to cause atrophy of the tissue outwardly of the band while yet allowing sufficient expansion upon stretching to permit placement over the scrotal pouch. These conditions require a band of approximately one to two inch diameter with substantial cross-sectional area approximating 0.1 square inch in relaxed condition for natural rubber and varying somewhat, depending upon the elastic nature of other eastomric material from which the band is formed. These parameters generally differ by several fold from the corresponding parameters of continuous elastic castration bands heretofore used for smaller immature animals or bands that are not stretched for placement and the parameters tend to dictate the nature of a tool used for their placement.

Since a continuous ligation band must allow passage of the scrotal pouch and contained testicular structure of an animal to be castrated through the orifice it defines, the instant band because of its small size must be enlarged by stretching to allow placement. The instant invention provides a tool to simply and easily accomplish the stretching of such bands of the required nature to a size and configuration that allows placement without damage to the elastic material. The tool provides a forward yoke supporting the band at two points, with a movable stretching rod communicating with the band at a third point between the first two support points to stretch the band in a triangular configuration for placement. To accomplish its purpose with a band of appropriate physical characteristics, the stretching rod requires substantial force that is provided by an associated compound lever operated tensioning mechanism that allows operation by a multiply smaller applied manual force for ease and simplicity of operation.

The problem of maintaining sufficient elastic tension to provide ligation by a continuous band that expands to create a large enough orifice to allow placement is solved by using a fastening clip to foreshorten the portion of the band about the neck of the animal's scrotal pouch. The foreshortened fastened portion of the tensed band then allows release of the tension created by the tool from both band portions to relax that band portion not extending about the scrotal pouch for removal of the tool. The deformable metallic fastening clip disclosed in my prior U.S. Pat. No. 5,188,637 is effective for fastening the band portion about the scrotal pouch.

The compound lever type operation of the tool provides a secondary benefit of speeding the individual castration process and allowing a single operator to accomplish a greater number of castrations in a given period of time than could be accomplished with various prior tools. In the modern practice of animal husbandry often groups of several hundred animals may be castrated over a short period of time in a continuous operation. With prior tools not providing compound leverage operation, the manual force required by a workman in operating various prior castration tools was often so great, and application of that force sufficiently difficult, that the process was tiring to a workman, and particularly his hand and wrist muscles, to such an extent that the workman's physical ability became a limiting factor in the number of sequential castrations that the workman could accomplish without substantial rest. This problem could be of such extent that it might cause permanent physical damage to a workman. The instant tool resolves this problem by requiring substantially less force that is of such nature that it is not unusually tiring or damaging to a workman to allow continuous operation over lengthy periods of time without adverse physiological effects that may cause injury or work slow down. The tool also may easily be motorized if desired.

My invention lies not in any of these features individually, but rather in the synergistic combination of all of the structures of my tool and steps of my process that necessarily give rise to the results flowing therefrom.

SUMMARY OF INVENTION

My tool provides an elongate body defining a perpendicularly depending handle at a first rearward end and a U-shaped band holding yoke with spaced extending forwardly legs at a second forward end. A compound band holdimg yoke of a first species provides opposed, pivotally mounted tip portions that are maintained in a first position to support a continuous elastic band at two spaced points for band tensioning, by control structure that may be operated to allow pivotal motion of the tip portions to a second position whereat the tensioned band is released from support on the band holding yoke. A tensioning rod communicates through the rearward portion of the band holding yoke to contact a third point on the band between the two support points on the band holding yoke to move one course of the band rearwardly to stretch and tension the band in a triangular configuration. The tensioning rod extends rearwardly to activating mechanism carried by the rearward portion of the body that provides a compound lever for moving the stretching rod rearwardly through a supporting block and a control lever that in a first null position allows only rearward motion of the rod, but is movable to a second position to allow forward motion of the tensioning rod to release tension in a supported band. A second species of band holding yoke provides a unitary structure with forward portions of the legs of the band holding yoke of particular shape that allow release of a supported band by manual manipulation of the band holding yoke relative to the band after placement.

In providing such mechanism, it is:

A principal object to provide a ligation type castration tool, for larger sexually mature animals having an external scrotal pouch, that stretches a small preformed continuous elastic ligation band sufficiently to allow passage of the scrotal pouch through the orifice defined by the stretched band, with subsequent fastening by a clip of a portion of the stretched band about the area of interconnection of the scrotal pouch with the body structure of the animal for ligation of the scrotal pouch and its contents.

A further object is to provide such a tool that has a band holding yoke with forwardly extending legs for two point support of the ligation band and a tensioning rod communicating forwardly between the yoke arms to attach to the ligation band at a third point between the yoke support points for tensioning of the band by motion of the tensioning rod away from the two band support points on the band holding yoke.

A further object is to provide such a tool that has compound lever mechanism to move the tensioning rod in a rearward direction and control structure that normally prevents forward motion of the tensioning rod but allows selective forward motion responsive to manipulation.

A still further object is to provide such a tool that in a first species has a compound band holding yoke with pivotally mounted tip portions that are maintained in a first position to support a ligation band during tensioning but may thereafter be moved to a second position to allow band release, and in a second species has a unitary band holding yoke with particularly shaped forward end portions of the yoke legs to release a ligation band by motion of the yoke away from the band.

A still further object is to provide a process for ligation castration of large mature animals having an external scrotal pouch that uses small continuous ligation bands that must be stretched to define an orifice of sufficient size to pass over the scrotal pouch of the animal.

A still further object is to provide such a tool that is of new and novel design, of rugged and durable nature, of simple and economic manufacture and is otherwise well suited to the uses and purposes for which it is intended.

Other and further objects of my invention will appear from the following specification and accompanying drawings which form a part hereof. In carrying out the objects of my invention, however, it is to be understood that its features are susceptible of change in design and structural arrangement, with only preferred and practical embodiments of the best known modes being illustrated in the accompanying drawings and specified as is required.

BRIEF DESCRIPTION OF DRAWINGS

In the accompanying drawings which form a part hereof and wherein like numbers of reference refer to similar parts throughout:

FIG. 1 is an isometric, rearwardly looking side view of my tool showing various of its parts, their configuration and relationship.

FIG. 2 is an isometric, rearwardly looking side view showing the opposite side of the tool illustrated in FIG. 1 from a different aspect.

FIG. 3 is a somewhat enlarged medial cross-sectional view of the tool of FIG. 1, taken on the offset broken line 3—3 thereon in the direction indicated by the arrows.

FIG. 4 is a partial isometric view of the forward portion of a tool such as illustrated in FIG. 1, but having a second species of unitary band holding yoke.

FIG. 5 is a somewhat enlarged isometric view of a continuous elastic ligation band with a fastening clip in operative position thereon.

FIG. 6 is a partial isometric view of the forward yoke portion of the tool of FIG. 2 showing a ligation band in place on and being stretched by the tool.

DESCRIPTION OF THE PREFERRED EMBODIMENT

My invention generally provides elongate body 9 having band fastening structure 10 in the forward portion of the body with yoke structure 11 extending forwardly therefrom and stretching mechanism 12 carried in the rearward portion of the body to extend forwardly to the yoke structure.

Body 9 provides elongate body beam 13 defining laterally extending fastening ears 14 in its rearward end portion for interconnection of a handle structure by fasteners 15 extending fastenably therebetween. The forward end portion of body beam 13 carries annular support 16 defining medial channel 17 extending therethrough to allow passage of a tensioning rod and interconnected elastic band while providing guidance limits for their positional maintenance and a chamber for containment and deformation of a fastening clip.

The rearward portion of body beam 13 interconnects handle body 18 carrying structurally joined depending handle 19. Handle body 18 defines forwardly extending connector plate 20, of similar peripheral configuration to fastening ears 14 of the body beam 13, to receive fasteners 15 extending in threaded engagement into the connector plate 20 to structurally interconnect the handle body and body beam. The handle body 18 defines medial cavity 21 to receive and carry portions of band stretching mechanism 12. The forward wall of handle body 18 defines tensioning rod hole 23 to allow slidable passage of a tensioning rod through the handle body. Handle 19 preferably supports forwardly extending grip portion 22 to make the handle more easily and comfortably grippable by a user.

Band fastening structure 10 of this tool is substantially the same as the structure disclosed in my prior U.S. Pat. No. 5,188,637 and the fastening clip 65 used in the structure is also substantially the same as the fastening clip there disclosed. The channel for holding the fastening clip 65 is defined by the appropriate configuration of the inner wall of annular support 16 that defines the medial channel 17 therein. The annular support 16 defines axially aligned slot 66 to allow passage of the forward part of crimping lever 67 therethrough to fastenably deform a fastening clip. The medial forward part of the crimping lever 67 is pivotally carried on pivot pin 68 supported in the lower forward portion of body beam 13 for pivotal motion to allow the forward part of the crimping lever to move through slot 66 and into medial channel 17 to crimp a fastening clip in the channel upon a fastening band passing through the fastening clip.

Yoke structure 11 provides a generally flat, U-shaped band holding yoke formed by back 24 interconnecting forwardly and laterally outwardly extending legs 25. Back 24 of the yoke is structurally carried by the forward end portion of body beam 13 immediately rearwardly of annular support 16. The forward outer end portions of each leg 25 carry band fastening dogs 26 pivotally mounted on the undersurface of the legs 25 by fasteners 27 extending through both elements. Each band fastening dog 26 defines fastening groove 28 on its forward laterally outer edge to aid positional maintenance of an elastomeric band extending between the fastening dogs and defines a rearwardly protruding fastening lug 29 on its laterally inner edge to aid positional maintenance of the fastening dog against rotation.

Band release yoke 30, 31 defined by back 30 and forwardly and laterally outwardly extending legs 31 is of a configuration similar to band holding yoke 24, 25 except that the forwardly extending legs are somewhat shorter to avoid interference with fasteners 27 of the band holding yoke. The band release yoke 30, 31 is carried for limited slidable motion in an elongate direction on the upper surface of the band holding yoke 24, 25 by plural threaded fasteners 32 extending through plural elongate slots 33 defined through the band release yoke and into threaded engagement in cooperating holes defined in appropriate positions in legs 25 of the band holding yoke, so that the band release yoke may move forwardly and rearwardly for a limited distance relative to the band holding yoke. Fastening pins 34 are carried by the forward portion of each leg 31 of the band release yoke 30, 31 to depend through elongate slots 69 defined in appropriate position in each leg 25 of the band holding yoke, and project spacedly beneath the band holding yoke to contact fastening lugs 29 of the band fastening dogs 26 for selective positional maintenance of the fastening dogs against rotation.

Back 30 of the band release yoke 30, 31 carries similar opposed upstanding release lever brackets 35 that support laterally extending release lever pin 36 therebetween. Angulated release lever 37 is pivotally carried on the release lever pin 36 rearwardly of annular support 16, with depending arm 37a adjacent to the annular support and manipulation arm 37b extending rearwardly and upwardly therefrom. With this structure as the angulated manipulation arm 37b is pivoted downwardly, the depending arm 37a will not move by reason of support against the rearward surface of annular support 16 and the band release yoke 30, 31 will responsively move rearwardly to remove support of fastening pins 34 from fastening lugs 29 to allow pivotal motion of the band fastening dogs 26 to release a tensioned elastic band supported between the fastening dogs.

Band stretching mechanism 12 provides elongate stretching rod 38 slidably supported in holding block 41 that is carried in medial cavity 21 defined in handle body 18. The stretching rod 38 has a length to extend from a point spacedly rearwardly of holding block 41 forwardly to the band fastening dogs 26. The stretching rod defines band holding notch 39 in its forward end portion and structurally carries "D" ring 40 in its rearward end portion to aid manipulation. The stretching rod is carried for slidable motion in channel 64 defined in holding block 41 and in channel 17 of annular support 16 for some positional restraint of its forward portion.

The stretching lever mechanism provides similar opposed mounting levers 42 pivotally carried on each side of holding block 41 by inner mounting bolt 43 extending therebetween and through the holding block. The mounting levers 42 carry medial mounting bolt 44 extending therebetween spacedly above the upper portion of holding block 41 to pivotally mount similar spaced rearwardly extending stretching rod levers 45 and the inner portion of stretching lever 46 therebetween. The outer end portions of mounting levers 42 carry outer mounting bolt 47 which extends pivotally through the medial portion of stretching lever 46. The rearward end portions of stretching rod levers 45 pivotally carry laterally extending stretching rod lever bolt 48 extending therebetween and pivotally through stretching lever block 49.

The stretching lever block 49 defines lower elongate channel 50 to slidably receive the stretching rod 38 which extends in an elongate direction through the stretching lever block 49 and an upper channel carrying canting lever fastener 51 to movably mount stretching lever block canting lever 52 forwardly of the block. Canting lever 52 depends from fastener 51 to define stretching rod hole 53 to allow movable passage of the stretching rod 38 therethrough. Compression spring 54 is carried about the stretching rod 38, between the rearward surface of canting lever 52 and an adjacent surface of stretching lever block 49, to bias the lower portion of the canting lever 52 forwardly. With this structure canting lever 52 will bind on the stretching rod 38 to require the stretching rod move rearwardly with rearward motion of the stretching lever block 49, but will allow free forward motion of the stretching lever block on the stretching rod responsive to motion of the stretching lever.

Stretching rod canting lever 55 is carried in handle chamber 21 between the forward portion of holding block 41 and the rearward surface of the handle body 18 that defines the forward surface of handle chamber 21. This canting lever 55 is vertically elongate with medial upper hole 56 defined therein to allow free slidable passage of stretching rod 38 through the canting lever. The upper portion of the forward wall of handle body 18 threadedly carries adjustment screw 57 to extend rearwardly through the handle body and into contact with the upper portion of canting lever 55 above hole 56 to provide an adjustably positional stop to limit the forward motion of the upper part of the canting lever. Compression spring 58 is carried below stretching rod 38 between canting lever 55 and the adjacent portion of holding block 41 to bias the lower portion of the canting lever 55 forwardly. With this structure the stretching rod 38 may freely move rearwardly through canting lever 55, but the canting lever prevents forward motion of the stretching rod by binding upon the rod by reason of a slight forwardly angulated relationship thereto. The stretching rod 38 may be released from this binding action to allow forward motion of the rod through the canting lever by moving the lower portion of the canting lever rearwardly, so that the lever assumes a substantially perpendicular position relative to the stretching rod and will not bind thereon.

A second species of simple band holding yoke 11A having a unitary structure is shown in FIG. 4. The body 9 and stretching mechanism 12 of this second species of yoke are the same as those members used with the first species 11 of yoke. The yoke 11A provides a simple unitary flat U-shaped structure defined by back 60 interconnecting similar forwardly and laterally outwardly extending legs 61. The forward end portions of legs 61 each define curvilinear band grooves 62 extending inwardly at the forward lateral portions of the legs to define band holding portions 63 extending forwardly from the laterally inward edges of the legs. An elastic band carried by this yoke is released by manual manipulation of the tool rather than by separate mechanical release structure such as provided in the first species by yoke 11.

Having described the structure of my tool, its operation may be understood.

A tool of the first species of FIGS. 1–3, constructed according to the foregoing specification, is provided with an appropriately constituted endless elastic band 59.

The elastomeric band 59 must be of such structure and elastic nature that when stretched about the neck of the scrotal pouch of an animal and there fastened, it has sufficient elastic force to cause ligation, and at the same time it must allow expansion sufficiently for passage of the scrotal pouch and contained testicular structure of a large mature animal such as a bovine bull through the orifice defined by the stretched band without breakage. The band must also provide sufficient material to allow fastening in a tensed condition by a deformable metallic fastening clip or similar fastening structure. Normally such a band formed of natural rubber will require a cross-sectional area of approximately 0.1 to 0.4 square inch when the cross-sectional configuration is of a rectangular form. Such a band normally will have a relaxed diameter of from approximately one to three inches. These parameters may vary generally with the nature of the elastomeric material and particularly for specific purposes while such bands remain operative for castration, and such variant bands are within the ambit and scope of my invention.

For use of the tool, band release yoke 30, 31 is moved to its forwardmost position and band fastening dogs 26 are rotated to a position whereat fastening lugs 29 are adjacent the associated fastening pins 34 in a position that prevents inwardly directed rotary motion of the forward portion of the band fastening dogs. With the fastening dogs 26 in this position elastic band 59 is manually placed on the band holding yoke 24, 25 to extend between fastening grooves 28 of the opposed band fastening dogs. Elastic band 59 and the band holding yoke preferably for convenience are configured so that when the band is placed between the fastening dogs it has some tension in it to create friction between the band and fastening dogs to aid positional maintenance of the band on the fastening dogs.

The lower portion of canting lever 55 is then moved rearwardly to allow forward motion of stretching rod 38 therethrough and the stretching rod is moved forwardly to the elastic band 59. One course of that band is inserted within band holding notch 39 of the stretching rod so that the band is maintained in that notch.

Stretching lever 46 is then manually operated with a reciprocating motion so that the rearward component of motion of the stretching lever will move stretching lever block 49 rearwardly, which in turn moves stretching rod 38 rearwardly by reason of the binding action of stretching rod canting lever 52 carried by the stretching lever block on the stretching rod. As the stretching lever 46 is moved forwardly the stretching lever block 49 will move forwardly on the stretching rod 38 because the stretching rod is prevented from forward motion by the binding force created on it by canting lever 55. This reciprocating stretching lever motion is continued until the stretching rod is moved rearwardly a distance sufficient to create a configuration in elastic band 59 that allows placement of the band over the scrotal pouch of an animal and creates appropriate tension in the band for ligation. It is to be noted that in this stretching rod motion the band holding notch 39 and the rearward portion of the elastomeric band 59 fastened therein will be moved rearwardly through channel 17 of annular support 16 and the channel of a fastening clip 65 carried therein.

The elastic band, while maintained in this stretched condition by the tool, is manually manipulated by means of the tool, and manipulation of the scrotal pouch of an animal if required, to pass the scrotal pouch and its contents through the orifice defined by the stretched band, which will be of a generally triangular shape within the yoke 11 by reason of its three point support by the yoke and the stretching rod.

With the elastomeric band 59 thusly placed, it is moved to the ligation site at the neck of the scrotal pouch adjacent the animals's body, and fastening clip 65, then extending about the band at a point adjacent to the band portion about the animal scrotal pouch, is crimped to fasten the band portion about the scrotal pouch together with the existing tension in it. The band portion not about the scrotal pouch is then released from the stretching rod 38 by moving the stretching rod forewardly and rotating it appropriately if necessary to allow the release of the portion of the band from holding notch 39. The band portion about the scrotal pouch is then released from the band holding yoke by moving the upper, rearwardly extending portion of release lever 37b downwardly to move band release yoke 30, 31 rearwardly. The rearward motion of the band release yoke responsively moves fastening pins 34 rearwardly and out of contact with the band fastening dogs 26 to allow rotation of the forward portion of the fastening dogs inwardly toward each other by reason of the tensioned band portion extending between them and thusly releases the elastic band from the yoke. The elastic band then will be in place in position on the animal to accomplish its ligation function and the portion not about the scrotal pouch may be trimed if desired. The tool may also be removed from a placed and fastened band by releasing the band portion about the scrotal pouch from the yoke in the same fashion as described and thereafter releasing the band portion carried by the stretching rod.

The placement of an elastomeric band with the second species of yoke of FIG. 4 is accomplished in the same fashion as described for the first species of FIGS. 1–3. After the band is tensioned, placed in proper position about the scrotal pouch and fastened by a clip as described, the stretching rod 38 is moved forwardly to release tension in the rearward band portion not about the scrotal pouch and the band is released from interconnection with the stretching rod. The tool then is manually manipulated by an operator to pull away from the tensioned portion of the band about the animal's scrotal pouch so that the band is released from support on the forward portions of the arms of yoke 11A and remains in place to accomplish its ligation function.

The foregoing description of my tool is necessarily of a detailed nature so that a specific embodiment of it might be set forth as required, but it is to be understood that various modifications of detail and rearrangement of parts might be resorted to without departing from its spirit, essence or scope.

Having thusly described my invention, what I desire to protect by Letters Patent, and what I claim is:

1. A tool for placement of a continuous elastic band about a body part of an animal for ligation, comprising in combination:

an elongate body having first forward and second rearward end portions with the first forward end portion carrying a forwardly extending band holding yoke having means for releasable attachment of a continuous elastic band at at least two spaced points and a second rearward end portion having handle means for manual manipulation of the body;

band stretching means carried by the second rearward end portion of the body for releasably attaching a portion of an elastic band and stretching the attached band portion rearwardly from the at least two spaced points for attachment of the band on the band holding yoke; and band fastening means carried by the first forward end portion of the body for fastening adjacent portions of an elastic band together spacedly rearwardly from the at least two spaced points for releasable attachment of the elastic band on the band holding yoke.

2. The tool of claim 1 wherein the band stretching means include an elongate stretching rod releasably communicating with the elastic band and compound lever means for moving the stretching rod rearwardly from the at least two spaced points for releasable attachment of the elastic band on the band holding yoke.

3. The tool of claim 1 wherein the band fastening means further comprise:

an annular support, carried by the first forward end portion of the body, defining a medial channel for passage of the stretching rod therethrough and for carrying an annular fastening clip therein; and a crimping lever movably carried by the body to extend into the medial channel of the annular support for crimping a deformable fastening clip carried in the medial channel.

4. A tool for placement by stretching of a continuous elastic band about the scrotal pouch of large sexually mature animals for ligation castration, comprising in combination:

an elongate body with a first forward end portion and a second rearward end portion carrying a handle body with a handle extending therefrom;

a band holding yoke, carried by the first forward end portion of the body, with spaced forwardly extending legs each having forward portions with means for releasably supporting a continuous elastic band extending about the forward portions of the legs;

band stretching mechanism carried by the second rearward end of the body having
      an elongate stretching rod supported for slidable motion in the handle body, and having means in a forward portion for releasably interconnecting a portion of a continuous elastic band thereto,
      compound lever means carried by the handle body for moving the stretching rod rearwardly, and
      release means carried by the handle body having a first state to prevent forward motion of the stretching rod and a second state to allow forward motion of the stretching rod; and fastening means carried by the body rearwardly of the band yoke for fastening adjacent portions of the continuous elastic band together.

5. The tool of claim 4 wherein the compound lever means for moving the stretching rod comprise:

a compound lever moving a stretching lever block slidably mounted on the stretching rod and carrying a stretching lever block canting lever extending about the stretching rod and biased to bind upon the stretching rod to move the stretching rod rearwardly when the stretching lever block is moved rearwardly, but allow slidable motion of the stretching lever block on the stretching rod in a forward direction.

6. The tool of claim 4 wherein the release means carried by the handle body comprise:

a stretching rod canting lever carried by the handle body and extending about the stretching rod, said stretching rod canting lever biased to a first position relative to the stretching rod to bind on the stretching rod to prevent forward motion of the stretching rod, but movable to a second position to allow forward motion of the stretching rod through the stretching rod canting lever.

7. The tool of claim 4 wherein the means for releasably supporting an elastic band about the leg of the band holding yoke comprise:

the band holding yoke having first and second sides with fastening dogs rotatably carried on the first side of the forward portion of each leg, each said fastening dog having first and second ends with means at the first end for support of the continuous elastic band and means at the second end to engage a fastening pin;

a band release yoke carried for slidable motion on the second side of the band holding yoke, said band release yoke having a fastening pin in the end portion of each leg projecting through slots defined in the band holding yoke and therepast to engage the second end of each band fastening dog to prevent rotary motion of the band fastening dogs when in a first position relative to the band holding yoke; and a release lever carried by the tool body to move the band release yoke to a second position relative to the band holding yoke to remove support of the fastening pins from the fastening dogs to allow rotation of the fastening dogs to release the elastic band carried by the fastening dogs.

8. A method for ligation of an animal body part with a continuous elastic band defining an orifice small enough that the body part to be ligated will not pass through the orifice defined by the band without stretching, comprising the steps of:

supporting the elastic band on two spaced supports to form two courses of the band extending between the two spaced supports;

moving a portion of one course of the elastic band between the two spaced supports away from the two supports to enlarge the orifice defined by the elastic band and create tension in the elastic band;

moving the streched elastic band about the body part to be ligated;

positioning the elastic band at a sight for ligation; and fastening the courses of the tensioned elastic band extending about the site for ligation to form a ligation band portion and a band portion not extending about the ligation site.

9. The method of claim 8 further comprising the steps of releasing the tension in the elastic band portion that is not fastened about the ligation site and trimming the elastic band portion that is not fastened about the ligation site spacedly adjacent to the ligation band portion.

10. The method of claim 8 wherein the step of fastening the two portions of the elastic band to form a ligation band portion comprises deforming a clip about the two band courses.

\* \* \* \* \*